Figure 1:
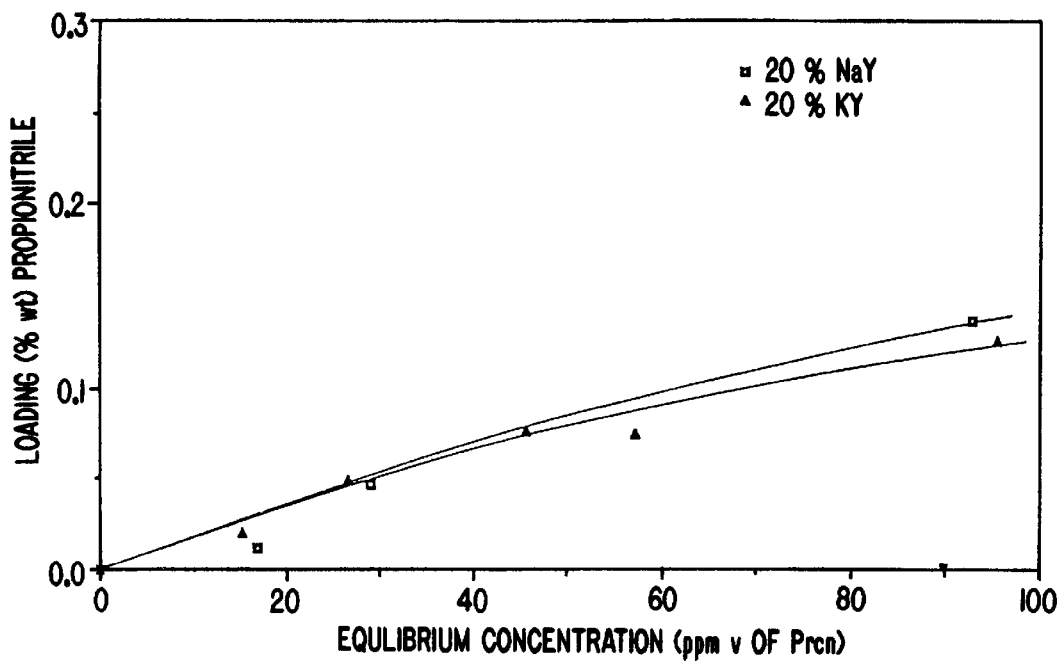

United States Patent [19]
Ramirez de Agudelo et al.

[11] Patent Number: 5,834,392
[45] Date of Patent: Nov. 10, 1998

[54] NITRILE SELECTIVE ADSORBENT

[75] Inventors: Maria Magdalena Ramirez de Agudelo; Julia Guerra; Marisela Gonzalez, all of Caracas, Venezuela

[73] Assignee: Intevep, S.A., Caracas, Venezuela

[21] Appl. No.: 529,759

[22] Filed: Sep. 18, 1995

[51] Int. Cl.$^6$ ............................................. B01J 29/06
[52] U.S. Cl. ................................ 502/64; 502/63; 502/68
[58] Field of Search .................................. 502/63, 64, 68

[56] References Cited

U.S. PATENT DOCUMENTS

| | | | |
|---|---|---|---|
| 4,822,762 | 4/1989 | Ellig et al. | 502/66 |
| 5,185,306 | 2/1993 | Cohn et al. | 502/66 |

OTHER PUBLICATIONS

Hawley; *Hawley's Condensed Chemical Dictionary* 12th edition p. 1108 1993 no month.

*Primary Examiner*—Steven Bos
*Assistant Examiner*—Thomas G. Dunn, Jr.
*Attorney, Agent, or Firm*—Bachman & LaPointe, P.C.

[57] ABSTRACT

An adsorbent for selective removal of nitrile from a hydrocarbon feedstock includes a substantially homogeneous mixture of a cationic nonacidic zeolite and an inorganic oxide matrix, the zeolite having an accessibility index of between about 0.1 to about 0.4, and the adsorbent being capable, when contacted with a hydrocarbon feedstock containing nitrile and containing dienes in an amount of at least about 1.0% by volume, of adsorbing at least about 80% of the nitrile during contact with at least about 200 volumes of the feedstock per volume of adsorbent.

10 Claims, 3 Drawing Sheets

NITRILE SELECTIVE ADSORBENT

BACKGROUND OF THE INVENTION

The invention relates to an adsorbent for selectively removing nitrile from a hydrocarbon feedstock, to a method for making the adsorbent, and to a process for removing nitrile from a hydrocarbon feedstock using the adsorbent.

Nitrile compounds are frequently undesirable contaminants in feedstocks which otherwise contain valuable fractions. Particularly, C4 and C5 cuts from FCC units can be useful in the preparation of oxygenates such as MTBE, ETBE, TAME and the like. However, these feedstocks typically contain nitrites and diolefins. The diolefins may typically be hydrogenated before and/or at the etherification reactor. Nitriles, however, must be removed upstream of the reactor and therefore must be removed in the presence of dienes which make the feedstock higly reactive.

Upstream nitrile removal techniques include washing, but propionitrile cannot be removed through washing. In the presence of hydrogenation catalysts, however, propionitrile is believed to undergo conversion to totally or partially hydrogenate products, which behave as basic nitrogen and rapidly poison the acid sites of the catalyst. It is apparent that the need remains for a treatment for removal of nitrile compounds, especially propionitrile, wherein the agent used for removal is selective to nitrile and has longevity toward the selective removal of nitrile especially in the presence of relatively large amounts of dienes.

It is therefore the primary object of the present invention to provide a nitrile selective adsorbent which is not rapidly deactivated during use, even in the presence of dienes.

It is a further object of the present invention to provide a method for preparing an adsorbent according to the present invention.

It is a still further object of the present invention to provide a process for treating a feedstock such as an FCC etherification feedstock with a nitrile selective adsorbent according to the invention so as to effectively and selectively remove nitrile compounds.

Other objects and advantages will appear herein below.

SUMMARY OF THE INVENTION

In accordance with the invention, the foregoing objects and advantages are readily attained.

An adsorbent is provided according to the invention which comprises a substantially homogeneous mixture of a cationic nonacidic zeolite and an inorganic oxide matrix, said zeolite having an accessibility index of between about 0.1 to about 0.4, and said adsorbent being capable, when contacted with a hydrocarbon feedstock containing nitrile and containing dienes in an amount of at least about 1.0% by volume, of adsorbing at least about 80% of said nitrile during contact with at least about 200 volumes of said feedstock per volume of adsorbent.

A method for making the adsorbent of the present invention is provided which method comprises the steps of providing a cationic nonacidic zeolite; providing an inert inorganic oxide matrix; washing said matrix with an alkaline hydroxide so as to provide a washed matrix having neutralized surface acidity; calcining said washed matrix so as to provide a calcined matrix having reduced surface hydroxide; mixing said zeolite and said calcined matrix so as to provide a substantially homogeneous mixture; forming said substantially homogeneous mixture into adsorbent elements; and calcining said adsorbent elements so as to provide said adsorbent.

A process for treating a hydrocarbon feedstock for removal of nitrile is provided which process comprises the steps of providing a hydrocarbon feedstock having a nitrile content of less than or equal to about 400 ppm; providing an adsorbent for selective removal of nitrile from a hydrocarbon feedstock comprising a substantially homogeneous mixture of a cationic nonacidic zeolite and an inorganic oxide matrix, said zeolite having an accessibility index of between about 0.1 to about 0.4; and contacting said feedstock and said adsorbent at nitrile adsorption conditions whereby at least about 80% of said nitrile content is adsorbed by said adsorbent during contact with at least about 200 volumes of said feedstock per volume of said adsorbent.

BRIEF DESCRIPTION OF THE DRAWINGS

A detailed description of preferred embodiments of the invention follows, with reference to the attached drawings, wherein:

FIG. 1 is an illustration of propionitrile adsorption isotherms for Example 2;

FIG. 2 is an illustration of propionitrile desorption isobars for Example 3;

FIG. 3 is an illustration of 1,3-pentadiene desorption isobars for Example 3;

FIG. 4 is an illustration of adsorption isotherms on Na zeolites for Example 4;

FIG. 5 is an illustration of adsorption isotherms on K zeolites for Example 4; and FIG. 6 is an illustration of results of the pilot plant test of Example 5.

DETAILED DESCRIPTION

The invention relates to an adsorbent for selectively removing nitrile from a hydrocarbon feedstock, to a method for preparing a nitrile selective adsorbent, and to a process for treating a hydrocarbon feedstock with a nitrile selective adsorbent for removal of nitrile contaminants contained therein.

According to the invention, a nitrile selective adsorbent is disclosed which comprises a substantially homogeneous mixture of a nonacidic cationic zeolite and an inorganic oxide matrix, preferably including a binder and being extruded or otherwise formed into a desired shape for use in hydrocarbon contacting processes. The zeolite is preferably selected so as to provide a high activity toward the adsorption of nitrile, and a low activity toward polymerization of dienes, while the matrix is preferably selected so as to have a high activity toward reversible adsorption of dienes, and a low activity toward the adsorption of nitrile. This combination of properties according to the invention provides the adsorbent with an advantageous and desirable selectivity toward the adsorption of nitrile compounds such as propionitrile when contacted with a nitrile containing feedstock, with a reduced tendency toward polymerization of dienes which can result in fouling of the adsorbent. Further, the activity of the adsorbent toward selective adsorption of nitrile is not rapidly deactivated during use.

The zeolite material of the adsorbent according to the invention is preferably selected from the group consisting of faujasite, mordenite, offretite, A-zeolite, erionite, L-zeolite, ST-5 zeolite, X-zeolite, Y-zeolite, and mixtures thereof. The zeolite is preferably nonacidic, and preferably is transformed or otherwise treated to contain cations selected from the group consisting of Li, Na, K, Cs, Mg, Ca, Sr, Ba and mixtures thereof, most preferably Na, K or mixtures thereof.

The zeolite is also preferably selected and prepared so as to have an accessibility index, which will be defined below, of between about 0.1 to about 0.4. The accessibility index is a gauge of the relative accessibility of the active pore sites of the zeolite to nitrile compounds and to other compounds such as dienes.

The inorganic oxide matrix according to the invention is preferably selected from the group consisting of silica, alumina, kaolin, clays, ceramics and mixtures thereof. The matrix material is preferably substantially inert, may be crystalline or amorphous, and is treated according to the invention so as to have substantially no surface acidity. It is also preferable that the matrix be cost-effective and moldable.

According to the invention, the zeolite and matrix materials are preferably present in the adsorbent in a ratio by weight of zeolite to matrix of between about 1:1 to about 1:100. In this range the amount of zeolite is further selected based upon the amount and type of contaminants involved, and the surface area of the zeolite. The adsorbent preferably has a surface area of between about 100 to about 1000 m$^2$/g, most preferably between about 200 to about 600 m$^2$/g, and has an overall surface acidity of less than or equal to about 2.7 mmol/g. The adsorbent according to the invention is selective toward the adsorption of nitrile compounds and is therefore useful in the selective removal of nitrile contaminants from a nitrile containing feedstock.

As set forth above, the zeolite material of the adsorbent of the present invention preferably has an accessibility index of between about 0.1 to about 0.4. In accordance with the invention the accessibility index represents a ratio of the molecular accessibility volume of the zeolite material for 2 parallel pentadienes to the molecular accessibility volume of the zeolite for propionitrile. It has been found according to the invention that adsorbents containing zeolites having an accessibility index as set forth above are particularly effective in the selective removal of nitrile without diene polymerization as desired. The measurement of molecular accessibility is further illustrated in Example 7 set forth below.

The adsorbent of the present invention is preferably prepared as follows. A zeolite material is provided, preferably selected from the group consisting of faujasite, mordenite, offretite, A-zeolite, erionite, L-zeolite, ST-5 zeolite, X-zeolite, Y-zeolite and mixtures thereof. The zeolite is preferably nonacidic, and has been transformed or otherwise treated so as to contain cations preferably selected from the group consisting of Li, Na, K, Cs, Mg, Ca, Sr, Ba and mixtures thereof, most preferably Na, K or mixtures thereof. These cations have been found according to the invention to allow access of nitrile compounds to the active sites of the zeolite while prohibiting entry of more than one molecule such as dienes and thereby preventing the polymerization of dienes as desired in accordance with the present invention.

According to the invention, a matrix material is provided which is preferably selected from the group consisting of silica, alumina, kaolin, clays, ceramics and mixtures thereof. The matrix is advantageously treated in accordance with the invention so as to reduce the surface acidity of the matrix substantially to nil. This may preferably be accomplished by washing the matrix material with an alkaline base wash material such as an alkaline hydroxide. The matrix is preferably washed with the alkaline hydroxide so as to neutralize the surface acidity of the matrix which has been found to be desirable in providing an adsorbent having the desired activity and longevity toward the selective removal of nitrile according to the invention. According to the invention, the alkaline hydroxide wash solution is preferably selected from the group consisting of NaOH, KOH, NH$_4$OH and mixtures thereof. After washing with the alkaline hydroxide, the matrix is preferably further washed, for example with water, so as to remove any remaining un-reacted alkaline hydroxide. The washed matrix is then preferably dried, for example overnight at a temperature of between about 80° to about 250° C., and then calcined, preferably at a temperature of between about 400° to about 850° C. so as to remove any remaining hydroxide (OH$^-$) on the surface of the matrix.

The washed and calcined matrix is then preferably mixed with the zeolite so as to provide a substantially homogeneous mixture thereof. As set forth above, the zeolite and matrix materials may preferably be provided in amounts sufficient to provide a ratio by weight of the zeolite to the matrix material of between about 1:1 to about 1:100.

Depending upon the desired form of the adsorbent end product, a binder material may preferably be added to the mixture so that the mixture can then be extruded or otherwise formed into a desirable shape or form, depending upon the type of process in which the adsorbent is to be used. A suitable binder material is Ludox™ although other binder materials may be suitable in accordance with the invention.

After extrusion, the extruded adsorbent elements are preferably dried, for example overnight at a temperature of between about 80° to about 250° C., and then calcined, preferably at a temperature of between about 400° to about 700° C., so as to provide the final adsorbent product according to the present invention.

The described method for preparing the adsorbent product according to the invention has been found to provide an adsorbent material having a desirably low surface acidity, preferably less than or equal to about 2.7 mmol/g, as measured by the amount of irreversibly adsorbed pyridine molecules on the surface of the adsorbent. The measurement of surface acidity is further described in Example 1 below. This low surface acidity has been found according to the invention to be particularly advantageous in providing an adsorbent having the desired selectivity toward adsorption of nitrile.

The adsorbent product according to the invention is especially useful in treating hydrocarbon feedstock containing up to about 400 ppm of nitrile, preferably between about 3 to about 1000 ppm as nitrogen, and at least about 1.0% dienes, preferably at least about 2.0% by volume of the feedstock. A particularly desirable feedstock is an FCC etherification feed, most preferably a C4–C7 cut of such a feed, which contains nitrile and diene contaminants. The adsorbent material according to the invention has been found to have excellent selectivity and longevity toward the removal of nitrile from such feedstocks.

The adsorbent product of the present invention may be used in a hydrocarbon contacting process as follows. A suitable feedstock is provided, as is an adsorbent according to the invention as set forth above. The feedstock and adsorbent are preferably contacted according to the invention in suitable treatment facilities, and under moderate nitrile removal conditions, most preferably at a temperature of less than or equal to about 300° C., and a pressure of less than or equal to about 500 psi. The adsorbent according to the invention has been found to be capable of adsorption of at least 80% of the nitrile contaminant of a feedstock containing in excess of about 1.0% dienes over a treatment period during which about 200 volumes of feedstock were treated per volume of adsorbent. Thus, the adsorbent according to the present invention has an excellent selectivity and longevity for use in selectively removing nitrile contaminants from feedstocks containing relatively large fractions of nitrile and diene compounds.

EXAMPLE 1

This example illustrates the measurement of surface acidity of a sodium-Y zeolite and a kaolin matrix in accordance with the invention. The surface acidity is measured by measuring the amount of irreversibly adsorbed pyridine on samples of the relevant material. The kaolin was washed with NaOH so as to reduce surface acidity in accordance with the invention. The zeolite and matrix were pretreated with pyridine at 30° C. and 100° C., and were calcined at various temperatures between about 400° C. to about 900° C., as shown in Table 1 below.

TABLE 1

| Material | Calc. Temp. (°C.) | Irreversible adsorption (mmol pyridine/g) | |
| --- | --- | --- | --- |
| | | 30° C. | 100° C. |
| Na-Y | 500 | 2.5 | 1.5 |
| | 600 | 2.7 | 1.7 |
| kaolin | 600 | 0.1 | 0.02 |
| | 800 | 0.1 | 0.0 |

As shown in Table 1, zeolite according to the invention illustrates a very weak acidity which is substantially unaffected by calcination temperature, and the matrix material after treatment according to the invention has substantially no acidity, even at very low pretreatment temperatures.

EXAMPLE 2

This example illustrates the adsorption of propionitrile from test solutions using two adsorbents according to the invention. Two adsorbents were prepared according to the invention having 20% wt Na—Y zeolite in kaolin, and having 20% wt K—Y zeolite in kaolin. The samples were placed in contact with test solutions containing various concentrations of propionitrile in pentane, and were allowed to reach equilibrium. Upon reaching equilibrium, the solutions were analyzed using gas chromatography and the amount of adsorbed propionitrile was determined. FIG. 1 illustrates the adsorption isotherms for the various test solutions. As shown in FIG. 1, both adsorbents effected significant reductions in propionitrile for various loadings of the test solution. Further, the size of the cation, K or Na, did not significantly affect the adsorption of propionitrile.

EXAMPLE 3

Figure 2:
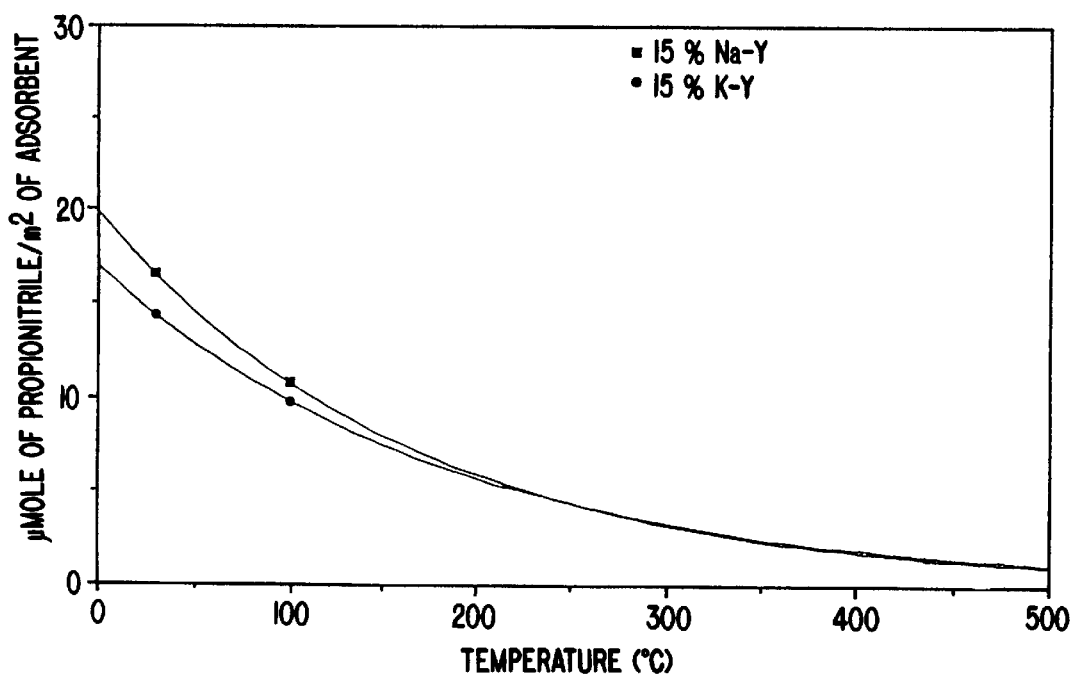
Figure 3:
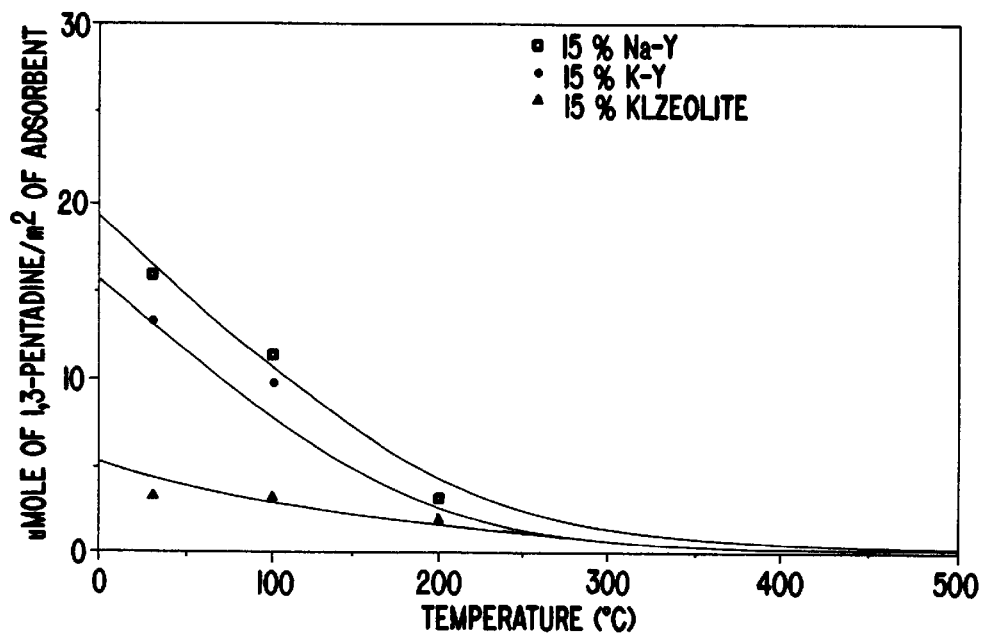

This example illustrates the desorption of nitrile and diene compounds from zeolites and matrix materials according to the invention. Two zeolite samples and a matrix sample were subjected to treatment of test solutions containing propionitrile and 1,3-pentadiene. The zeolite samples were a 15% wt Na—Y zeolite and a 15% wt K—Y zeolite, and the matrix sample was kaolin. After extended contact, these samples were regenerated using a desorption procedure at various temperatures. The propionitrile and 1,3-pentadiene desorption isobars were evaluated from the gas phase by thermogravimetric analysis at atmospheric pressure. FIGS. 2 and 3 illustrate the desorption isobars. As shown in FIG. 2, the zeolite samples exhibited an excellent desorption for propionitriles. FIG. 3 shows that the diene adsorption of the matrix is readily reversible. This example also clearly demonstrates the effect of the cation present in the zeolite in controlling the entrance of larger molecules such as the dienes into the zeolite cage. This activity of the cation serves to give the zeolite its desired selectivity toward adsorption of nitrile. Thus, certain combinations of cation and zeolite may be selected according to the invention to provide nitrile selectivity depending upon the various sizes of the nitrile, diene and cation molecules and the size of the zeolite apertures. For example, by comparing FIGS. 1 and 3, it can be seen that substituting K cations in place of Na cations does not significantly affect nitrile adsorption, but does change pentadiene adsorption, thereby increasing selectivity toward nitrile.

EXAMPLE 4

Figure 4:
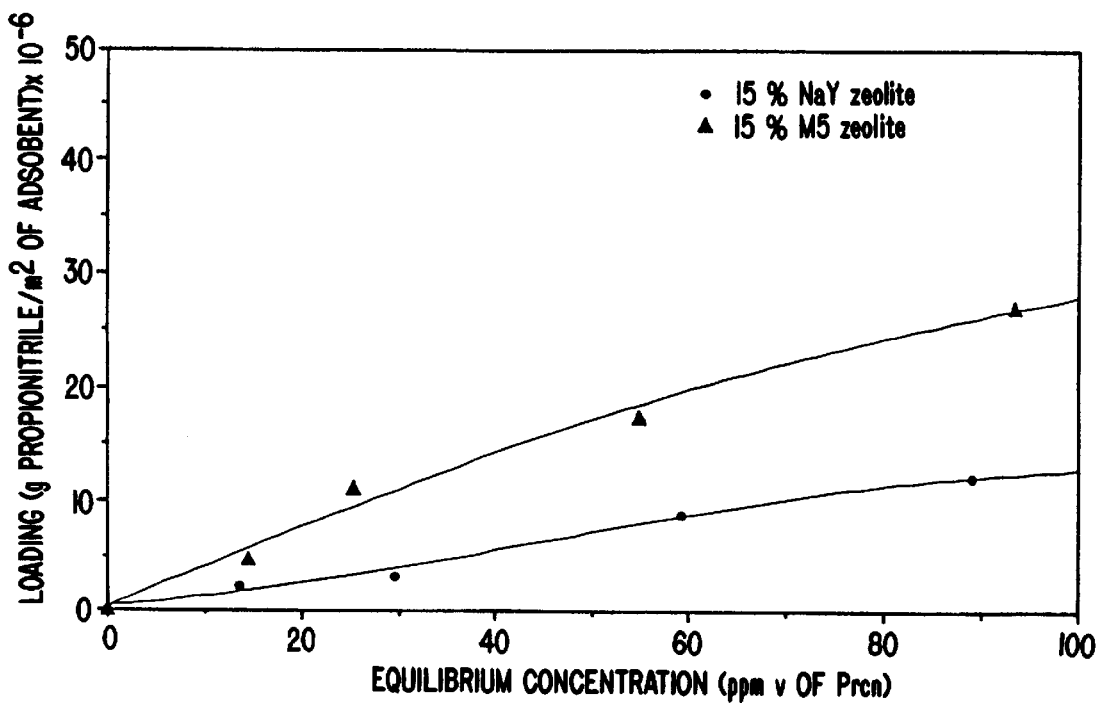
Figure 5:
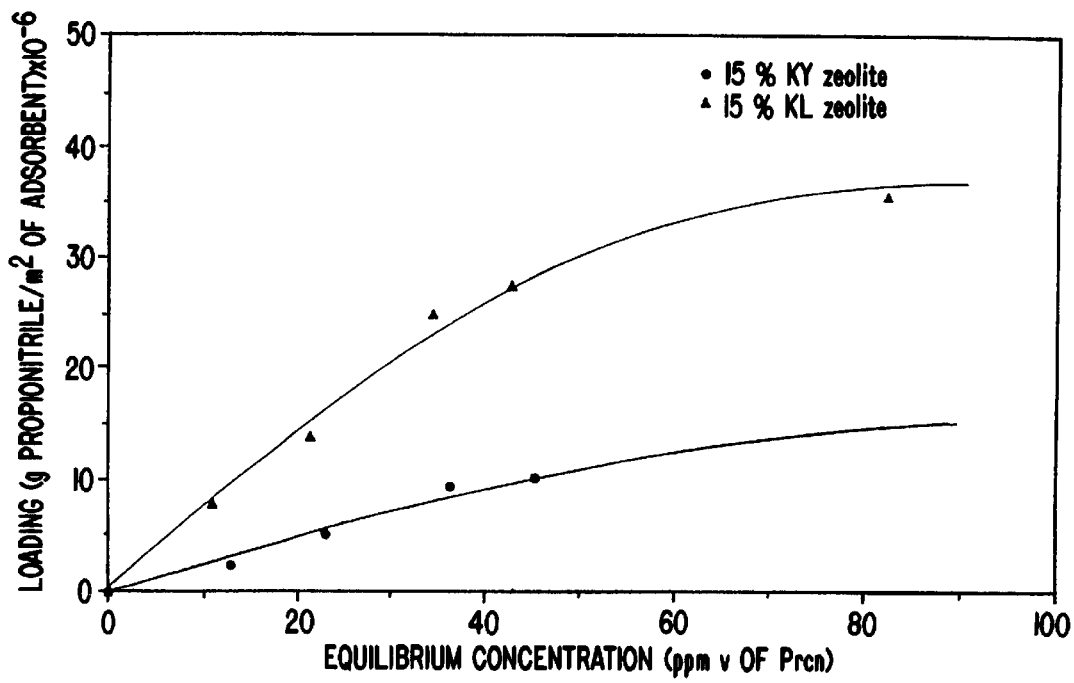

This example illustrates the selective adsorption of nitrile with several different zeolites. Several adsorbent samples were prepared and evaluated with test solutions as in Example 2. The samples tested were a 15% wt Na—Y zeolite in kaolin, a 15% wt Na—mordenite in kaolin, a 15% wt K—Y zeolite in kaolin, and a 15% K—L zeolite in kaolin. FIGS. 4 and 5 illustrate the adsorption isotherms for the various samples tested, and show the effect of using zeolites having different surface areas in accordance with the invention. FIG. 5 illustrates the advantage of K—Y zeolite over K—L zeolite in this application wherein K—Y zeolite adsorbs more nitrile than K—L zeolite, with a reduced adsorption of pentadiene. These examples illustrate that the proper selection of cation, zeolite and matrix in accordance with the invention can be manipulated so as to control the selectivity of the adsorbent to nitrile removal, particularly by avoiding factors that favor diene polymerization, namely bimolecular diffusion and acidity.

EXAMPLE 5

This example compares the selectivity for nitrile removal of a 40% wt. Na—Y zeolite in kaolin adsorbent extruded using Ludox™ as a binder according to the present invention, and several commercial adsorbents, namely, Selexsorb CD (0.7% diene), INTGARD-A (0.7% diene) and Selexsorb CD (<0.1% diene). The feedstock was a C5–C6 FCC cut having a composition as shown in Table 2 below.

TABLE 2

| Feedstock Composition | |
| --- | --- |
| C4 | 2.1% |
| C5 | 20.7% |
| C6 | 53.4% |
| C7 | 21.6% |
| diene | 2.0% |
| nitrile | 9.6 N ppm |
| basic nitrogen | 1.5 ppm |
| total sulfur | 244 ppm |

Figure 6:
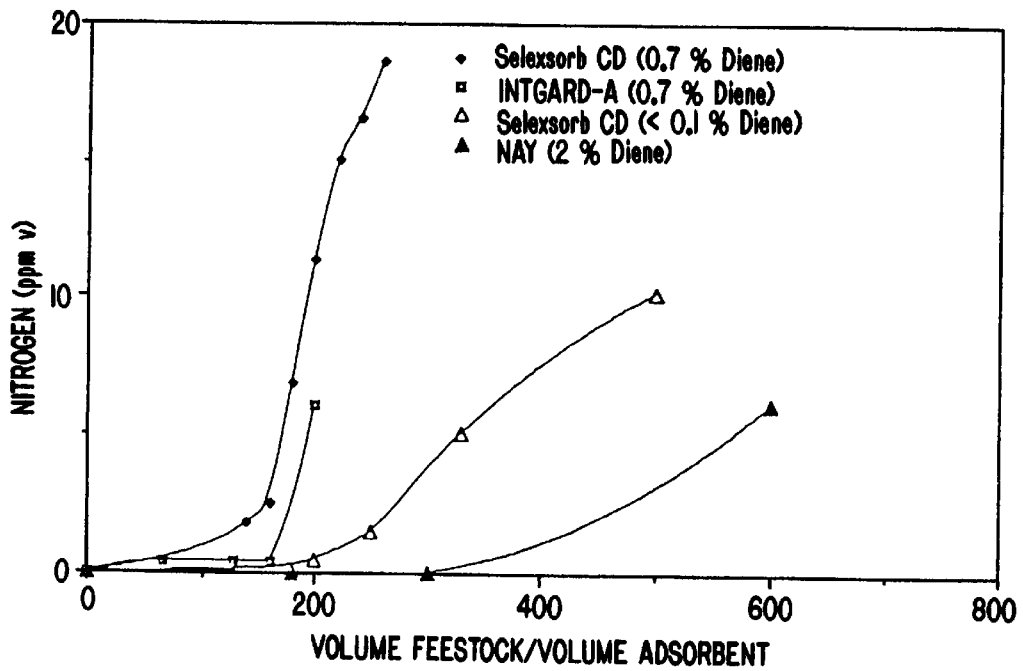

The feedstock and the various adsorbents being tested were contacted in a pilot plant under identical conditions, and the results are set forth in FIG. 6. As shown, the adsorbent of the present invention clearly outperforms the commercial adsorbents in both selectivity and longevity with respect to nitrile removal.

EXAMPLE 6

This example illustrates the preparation of an adsorbent according to the invention. A fully exchanged Na—Y zeolite and a kaolin matrix are provided. The kaolin was washed with NaOH so as to neutralize the existing surface acidity of the kaolin matrix. The neutralized matrix was then washed with water until remaining un-reacted NaOH was removed. The wet washed kaolin was then dried overnight at temperatures between 80° and 250° C., and the dried kaolin was then calcined at temperatures between 400° and 850° C. until all surface OH groups were removed. The calcined kaolin was then mixed with the zeolite so as to provide a homogeneous mixture thereof, and peptized alumina was added to the mixture as a binder. The combination of mixture and peptized alumina was then extruded so as to provide adsorbent elements of the desired size and shape, and the adsorbent elements were dried overnight at temperatures between 80° and 250° C. The dried adsorbent elements were then calcined at temperatures between 400° and 700° C. to obtain the desired nitrile selective adsorbent according to the invention.

EXAMPLE 7

This example illustrates the measurement of the accessibility index for several zeolites in accordance with the invention. Three zeolites, namely Y-zeolite, mordenite and L-zeolite, were each evaluated when loaded with Na and K cations respectively. The molecular accessibility of these zeolites with respect to propionitrile, pentadiene, I(2 lineal pentadiene mol) and II(2 parallel pentadiene mol) was determined using the Catalysis (TM) program from Biosym Technologies Inc. The results of these measurements are set forth below in Tables 3 and 4. Both linear and parallel arrangements for the dienes were considered in order to evaluate the possibility of polymerization. The data set forth in Tables 3 and 4 illustrate that the zeolite according to the invention will adsorb more nitrile than dienes, and that the potential for diene polymerization (by getting at least two diene molecules together) is reduced.

TABLE 3

| | (# molecules per unit cell) | | | | | |
|---|---|---|---|---|---|---|
| | Na-Y | K-Y | Na-Mor | K-mor | Na-L | K-L |
| propionitrile (A) | 181 | 153 | 21 | 19 | 16 | 16 |
| pentadiene | 128 | 124 | 19 | 15 | 14 | 12 |
| I(2 lineal pentadiene mol) | 54 | 53 | 10 | 10 | 9.3 | 9.7 |
| II(2 parallel pentadiene mol) (B) | 51 | 45 | 5 | 7 | 6 | 4.8 |
| Accessibility index (B/A) | 0.28 | 0.29 | 0.23 | 0.36 | 0.38 | 0.30 |

TABLE 4

| | (# molecules per g. zeolite) | | | | | |
|---|---|---|---|---|---|---|
| | Na-Y | K-Y | Na-Mor | K-mor | Na-L | K-L |
| propionitrile (A) | 14.4 | 11.5 | 7 | 6.1 | 6.8 | 6.4 |
| pentadiene | 10.2 | 9.3 | 6.3 | 4.8 | 6.1 | 4.8 |
| I(2 lineal pentadiene mol) | 4.3 | 3.9 | 3.3 | 3.3 | 3.9 | 3.9 |
| II(2 parallel pentadiene mol) (B) | 4.1 | 3.4 | 1.7 | 2.3 | 2.5 | 1.9 |
| Accessibility index (B/A) | 0.28 | 0.30 | 0.24 | 0.38 | 0.37 | 0.30 |

Thus disclosed is an adsorbent, a method for preparing an adsorbent, and a process for using the adsorbent for selective removal of nitrile from a nitrile containing feedstock wherein the adsorbent has an excellent selectivity and longevity toward the removal of nitrile compounds even in the presence of relatively large amounts of dienes.

It should also be noted that the characteristics of the adsorbent of the present invention are also well suited to use of the adsorbent as a catalyst support.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. An adsorbent for selective removal of nitrile from a hydrocarbon feedstock, comprising: a substantially homogeneous mixture of a cationic nonacidic zeolite and an inorganic oxide matrix, said zeolite having an accessibility index of between about 0.1 to about 0.4 wherein the accessibility index represents a ratio of the molecular accessibility volume of the zeolite material for 2 parallel pentadienes to the molecular accessibility volume of the zeolite for propionitrile, and said adsorbent being capable, when contacted with a hydrocarbon feedstock containing nitrile and containing dienes in an amount of at least about 1.0% by volume, of adsorbing at least about 80% of said nitrile during contact with at least about 200 volumes of said feedstock per volume of adsorbent.

2. An adsorbent according to claim 1, wherein said zeolite is selected from the group consisting of faujasite, mordenite, offretite, A-zeolite, erionite, L-zeolite, ST-5 zeolite, X-zeolite, Y-zeolite and mixtures thereof.

3. An adsorbent according to claim 1, wherein said zeolite contains at least one cation selected from the group consisting of Li, Na, K, Cs, Mg, Ca, Sr, Ba and mixtures thereof.

4. An adsorbent according to claim 1, wherein said zeolite contains at least one cation selected from the group consisting of Na, K and mixtures thereof.

5. An adsorbent according to claim 1, wherein said matrix is selected from the group consisting of silica, alumina, kaolin, clays, ceramics and mixtures thereof.

6. An adsorbent according to claim 1, wherein said matrix has substantially no surface acidity.

7. An adsorbent according to claim 1, wherein said zeolite and said matrix are present in a ratio by weight of zeolite to matrix of between about 1:1 to about 1:100.

8. An adsorbent according to claim 1, wherein said adsorbent has a surface area of between about 100 to about 1000 m$^2$/g.

9. An adsorbent according to claim 1, wherein said adsorbent has a surface area of between about 200 to about 600 m$^2$/g.

10. An adsorbent according to claim 1, wherein said adsorbent has a surface acidity of less than or equal to about 2.7 mmol/g.

* * * * *